United States Patent [19]

Henniger et al.

[11] Patent Number: 4,528,135

[45] Date of Patent: Jul. 9, 1985

[54] PROCESS FOR THE PREPARATION OF PENICILLANIC ACID 1,1-DIOXIDES

[75] Inventors: Peter W. Henniger, Leiden; Johannes K. van der Drift, Delft; Jagdish C. Kapur, Delft; Herman P. Fasel, Delft, all of Netherlands

[73] Assignee: Gist-Brocades N.V., Delft, Netherlands

[21] Appl. No.: 486,403

[22] Filed: Apr. 19, 1983

[30] Foreign Application Priority Data

Apr. 19, 1982 [GB] United Kingdom ............... 8211301

[51] Int. Cl.³ .......................................... C07D 499/00
[52] U.S. Cl. ...................... 260/245.2 R; 260/245.2 T
[58] Field of Search ................ 260/245.2 R, 245.2 T; 424/274, 270

[56] References Cited

U.S. PATENT DOCUMENTS 4,164,497  8/1979  Kamiya et al. ............... 260/245.2 R
4,419,284  12/1983  Crawford et al. ............ 260/245.2 R
4,444,687  4/1984  Gottstein ..................... 260/245.2 R

*Primary Examiner*—Nicholas S. Rizzo
*Attorney, Agent, or Firm*—Charles A. Muserlian

[57] ABSTRACT

A process for the preparation of penicillanic acid-1,1-dioxides of the formula

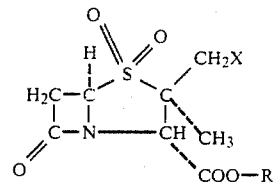

wherein X is selected from the group consisting of hydrogen and substituent such as halogen or acetoxy and R is selected from the group consisting of hydrogen, a pharmaceutically acceptable metal ion and/or ester radical comprising debrominating a 6-α-bromo- and/or 6,6-dibromo-penicillanic 1,1-dioxide selected from the group consisting of the formula

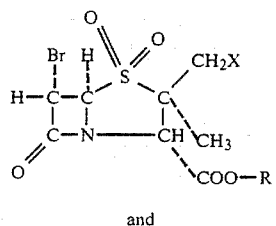

and

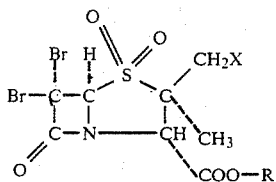

wherein X and R have the above definition in an aqueous containing medium with zinc in association with an acid having a pK$_a$-value measured in water less than 3.5 and optionally if R is H converting the acid into a pharmaceutically acceptable salt or ester.

10 Claims, No Drawings

PROCESS FOR THE PREPARATION OF PENICILLANIC ACID 1,1-DIOXIDES

STATE OF THE ART

The association of resistance of certain bacteria to β-lactam antibiotics has led to an intensive search for β-lactamse inhibitors. It is well-known that penicillanic acid-1,1-dioxide and derivatives thereof having substituents at the β-lactam methylene carbon atom and salts and esters thereof have useful pharmacological properties, for example as effective inhibitors of several types of β-lactamses present in various kinds of bacteria. They can be administered orally or parenterally and are described in U.S. Pat. No. 4,276,285 and Netherlands patent applications Ser. No. 78-06126 and 80-01285.

Dutch application Ser. No. 78-06126 describes the preparation of 6-α-bromo-penicillanic acid by diazotization-bromination of 6-β-amino-penicillanic acid as well as a reduction or debromination of the said 6-α-bromo compound with hydrogen in the presence of a palladium catalyst to obyain penicillanic acid of the formula

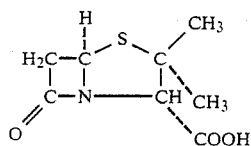

V followed by oxidation of the latter such as with 3-chloroperbenzoic acid or with a permanganate such as potassium permanganate to obtain penicillanic acid-1,1-dioxide (hereafter referred to as PAS).

The said reduction or debromination with a palladium catalyst and hydrogen is described both in said Netherlands patent application and British Pat. No. 1,072,108 and is uneconomical and not commercially practicable since the presence of an unprotected thioether group in the 5-membered ring of the 6-α-bromo and 6,6-dibromo-penicillanic acids requires the use of large amounts of catalyst, frequent repetition of the reduction sequence with a fresh amount of catalyst and prolonged reaction times and hydrogen pressure greater than atmospheric. The applicants of the present application were unable to obtain an average of about 10% yields with at best no more than 15% in many attempts to repeat the process at 0.3 moles scale of the said Netherlands patent application No. 78-06126. "Overall yield" is the yield calculated or the 6-β-amino-penicillanic acid starting material.

Netherlands patent application Ser. No. 80-01285 describes an overall yield increase by reversal of the last two steps. It has been ascertained that reduction of a mixture of compounds of the formulae

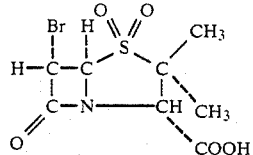

VI and

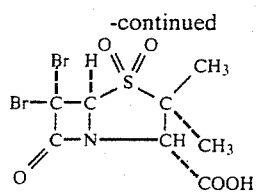

VII in the last step was associated with the use of only about one fifth of the amount of catalyst working under a pressure above atomspheric but significantly less than that hitherto employed and with less frequent repetition of the reduction sequence. However, although employing a thoroughly worked out procedure for the oxidation with permanganate of 6-α-bromo-penicillanic acid to form the compounds of formula VI by this method is associated with yields of approximately 80% or better and oxidation of the useful but usually rather small amount of the by-product 6,6-dibromo-penicillanic acid goes with less good yield—the overall yield of PAS, the compound of formula I wherein X is hydrogen, still could not be raised above a maximum of 20%. It was found as a result of extensive research and experimentation that the poor overall yield is not only caused by inadequate prior art diazotisation-bromination procedure, but also by insufficient result of the palladium catalyzed reduction step, and this may be inferred as being so as Dutch Patent Application No. 80-01285 mentions other reduction methods such as reduction with a trialkyl tin hydride such as tributyl tin hydride and also, though in a very inconspicuous fashion, zinc in acetic acid, formic acid or a phosphate buffer.

In view of the necessity to develop an economic and industrially applicable synthesis for PAS, it is apparent that tributyl tin hydride is an impossibly expensive reagent, which moreover is less suited for reduction of acid intermediates, while reduction with zinc in a phosphate buffer does not result, so we have found, in better yields than that obtained by reduction with a palladium catalyst, and reduction with zinc in acetic acid, although producing relatively somewhat tangibly better yields, is not very satisfactory also.

OBJECTS OF THE INVENTION

It is an object of the invention to provide a simple method of reducing compounds of formulae III and IV with substantially quantitative yields.

This and other objects and advantages of the invention will become obvious from the following detailed description.

THE INVENTION

The novel process of the invention for the preparation of penicillanic acid 1,1-dioxides of the formula

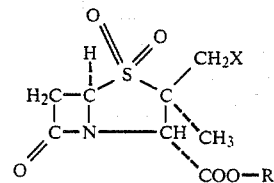

II wherein X is selected from the group consisting of hydrogen and substituent such as halogen or acetoxy and R is selected from the group consisting of hydrogen, a pharmaceutically acceptable metal ion and/or ester radical comprising debrominating a 6-α-bromo- and/or 6,6-dibromo-penicillanic 1,1-dioxide selected from the group consisting of the formula

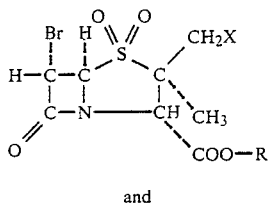

and

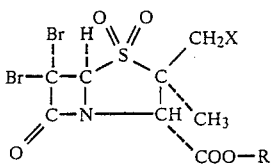

wherein X and R have the above definition in an aqueous containing medium with zinc in association with an acid having a $pK_a$-value measured in water less than 3.5 and optionally if R is H converting the acid into a pharmaceutically acceptable salt or ester.

The said process results in the preparation of penicillanic acid compounds of the formula

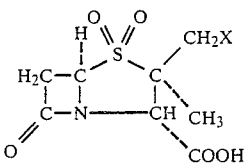

wherein X is hydrogen or a substitutent such as a halogen, preferably chlorine which is described in Netherlands patent application Ser. No. 81-00209 or acetoxy and the pharmaceutically acceptable acid salts or esters thereof. The compound of formula I wherein X is hydrogen is PAS.

Examples of suitable pharmaceutically acceptable salts of the acids of formula I are alkali metals such as sodium and potassium, alkaline earth metals such as calcium and magnesium, ammonium and substituted ammonium salts such as salts of such non-toxic, amines as trialkylamines like triethylamine, procaine, dibenzylamine, N-benzyl-β-phenethylamine, 1-ephenamide, N,N'-dibenzyl-ethylenediamine, dehydroabietylamine, N,N'-dibenzyl-ethylenediamine, dehydroabietylamine, N,N'-bis(dehydroabietyl)ethylenediamine, N-(lower)alkylpiperidine (e.g. N-ethylpiperidine) and other amines which have been used to form pharmaceutically acceptable salts of penicillins and cephalosporins. The most preferred salts are the alkali metal salts, i.e. the sodium and potassium salts, and the ammonium salts.

The esters of the acids are preferably those which are pharmaceutically acceptable and are known in the art to hydrolyze to the free acid in vivo. Preferred esters are those with an alkylcarbonyloxymethylene residue in which the hydrogen atom(s) of the methylene unit are optionally replaced by one or two methyl or ethyl groups and the alkyl group contains 1 to 5 carbon atoms, in particular pivaloyloxymethyl, or phthalid-3-yl esters.

The main object of the present invention is to provide an economically viable (possible "one-pot"), industrially applicable process for the preparation of penicillanic acid 1,1-dioxides of formula I and salts and esters thereof.

In broad outline, one aspect of the present invention is concerned with a process for the preparation of penicillanic acid-1,1-dioxides of the formula

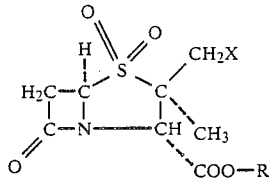

wherein X is as defined above and R is hydrogen or a pharmaceutically acceptable ester as is known in the penicillin field such as those mentioned above starting from a 6-α-bromo- and/or 6,6-dibromopenicillanic acid-1,1-dioxide derivative of the formula

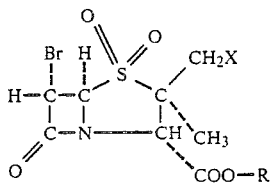

and

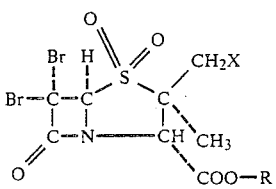

wherein X and R are as defined above and debrominating such compounds in the 6-position to obtain a compound of formula II, and optionally converting the acid (R=H) so obtained into a pharmaceutically acceptable salt or ether.

An attractive method to prepare these starting bromocompounds is disclosed in the U.S. patent application Ser. No. 486,981 filed on even date herewith entitled "Preparation of 6-α-bromo- and/or 6,6-dibromopenicillanic acid-1,1-dioxides", the contents of which are incorporated herein by reference. The said process comprises diazotising a 6-α-amino-penicillanic acid-1,1-dioxide and brominating the resulting diazotized compound.

The process of the invention surprisingly is a very simple reduction process for compounds of the formulae III and IV resulting in nearly quatitative yields (i.e. about 90%) of PAS and is achieved by reduction with zinc and an acid having a $pK_a$-value measured in water of less than 3.5, preferably hydrochloric acid, hydrobromic acid, citric acid or sulfuric acid, at a controlled pH of 2.5 to 6, and more preferably 3 to 5. Most preferably, hydrochloric acid, hydrobromic acid or sulfuric acid is used.

It will be appreciated by persons skilled in the art that the advantage of this reduction method is clearly shown by the fact that the overall yield calculated on 6-β-aminopenicillanic acid-1,1-dioxide as starting material from which the bromo-compounds are prepared according to the process of the copending application above mentioned is 60–70% while the Cignarella diazotization-bromination procedure discussed in Dutch application No. 80-01285 and an appropriate procedure for the oxidation with permanganate affords an overall yield of 33–38% with a possible maximum of 40%.

The reduction method of the invention will be elaborated hereafter. One of the major aims in the investigation leading to the present invention was to create a highly rewarding, practical, simple and economic method for the reduction of the bromides of formulae III and IV into the final products of formula II. It will be appreciated that, in view of the already disclosed material in the prior art, for instance in Dutch Patent Applications No. 80-01285 and No. 78-06126, and in the non-prepublished, older Dutch Patent Application No. 81-00209 which deal with the preparation of a related compound, i.e. PAS substituted in the β-methyl group with chlorine, employing in a preferred embodiment a concomitant substitution of the bromine atom and of the protecting 2,2,2-trichloroethyl group for hydrogen by means of zinc powder in a mixture of acetic acid and dimethylformamide resulting in a yield of only 37% the desired 2-β-chloromethyl-2-methyl-penam-3-carboxylic acid 1,1-dioxide starting from 2,2,2-trichloroethyl 6-α-bromo-2-β-chloromethyl-2-methylpenam-3-carboxylate 1,1-dioxide, as may be derived from e.g. Example XXII, step 4, page 31 in accordance with reaction scheme V of the last formula page, and eventually arising really satisfactory reduction method for the replacement of bromine atoms in compounds of formulae III and IV in the present invention will be characterized by narrowly defined conditions.

The resulting, unexpectedly and surprisingly effective method of reduction with zinc metal, e.g. finely divided zinc powder, is indeed associated with narrowly definable reaction conditions. Thus, when R is hydrogen:

in water, optionally diluted with an inert organic solvent such as acetonitrile, methyl acetate or ethyl acetate, in the latter cases involving reduction in a two-layer system; preferably an amount of at least 5% of water is used;

at pH 2.5 to 6, preferably between pH 3.5 and 5;

while adding, preferably in a continuous fashion, an acid having a $pK_a$-value in water of less than 3.5, more preferably dilute hydrochloric or hydrobromic acid or sulfuric acid, to maintain a pH of 2.5 to 6, preferably 3.5 to 5;

at a temperature, which may vary between 0° and 20° C., but preferably not higher than 15° C. for the monobromide and preferably not higher than 10° C. for the dibromide of formula IV;

with generally zinc metal, but preferably finely divided zinc powder;

with, with respect to the number of introduced bromine atoms, about 1.2 to about 2 moles of zinc for the reduction of 1 mole of the monobromide of formula III and about 2.4 to about 4 moles of zinc per mole of dibromide of formula IV, the minimum excess of approximately 20% relating to ideal situations, wherein (nearly) pure compounds of formulae III and/or IV are reduced in relatively concentrated solution, while substantially greater excesses are employed in cases of greater dilution or in cases wherein the number of manipulations after the diazotisation-bromination reaction is reduced considerably.

Acids having a $pK_a$-value in water of less than 3.5 other than dilute hydrochloric, hydrobromic and sulfuric acids which can be employed in conjunction with zinc in the reduction step are, for example, perchloric acid, aryl sulfonic acids such as p-tolylsulfonic acid and sufficiently acidic alkanoic acids, alkanoic diacids such as malonic acid and citric acid.

Starting from the dibromide of formula IV wherein R is hydrogen, the conversion yield as well as the actual isolation yield of practically pure compound of formula I is at least 85% and usually about 90%. Starting from the monobromide of formula III wherein R is hydrogen, the conversion yield is close to 100%, allowing isolation yields of 95% or more of substantially pure product.

If R is other than hydrogen, the reaction conditions are essentially the same, except that, although other water-miscible or partly water-miscible solvents such as methyl acetate and ethyl acetate can be used, the preferred main solvent is acetonitrile containing a sufficient but small amount of water, i.e. about 10% by volume, to establish sufficient contact in the heterogeneous reaction between zinc, acid and dissolved brominated substrates. When R is other than hydrogen, it is immaterial whether the substrate is a monobromide or a dibromide since in both cases the conversion yields as well as the actual isolation yields of substantially pure product are well above 85%.

Apart from being highly rewarding, economical and easy to manipulate, this surprisingly efficacious reduction method is also associated with simple isolation procedures as well as with the fortuitous circumstance, that during the reduction, by-products are to a large extent converted to virtually non-extractable compounds. Therefore, even when starting from substantially impure bromo-derivatives, an uncomplicated extraction procedure already results in substantially more pure final products, especially in the case when R is hydrogen.

The afore described particular method for the debromination of 6-bromo- and 6,6-dibromopenicillanic acid derivatives of formulae III and IV is unique and gives better yields than procedures hitherto disclosed in the prior art, for example that referred to hereinbefore, for the debromination of any 6-bromo- and/or 6,6-dibromopenicillanic acid compounds, especially when the reduction reagent is zinc in association with the cheap, commercially available hydrochloric acid, hydrobromic acid or sulfuric acid.

In the following examples there are described several preferred embodiments of the invention. However, it is to be understood that the invention is not intended to be limited to the specific embodiments.

EXAMPLE 1

Reduction of a crude mixture of 6,6-dibromopenicillanic acid 1,1-dioxide and 6-α-bromo-penicillanic 1,1-dioxide to penicillanic acid-1,1-dioxide STEP A: Crude mixture of 6,6-dibromo-penicillanic acid 1,1-dioxide and 6-α-bromo-penicillanic acid-1,1-dioxide 2.9 ml of concentrated sulfuric acid were added carefully to 25 ml of iced water and 3 ml of the thus prepared dilute sulfuric acid were added to 30 ml of acetonitrile at 0°–5° C. The amount of sulfuric acid employed was therefore about 10.5 mmol or 21 acid equivalent.

Continuously operating at temperatures between 0° and 5° C., 2.0 g (assumed to be equivalent to 8.0 mmol; in actual fact, only about 7.5 mmol) of 6-β-amino-penicillanic acid 1,1-dioxide were introduced with stirring which did not result in a complete dissolution and then 8 g (25 mmol) of pyridine hydrobromide perbromide ($C_5H_5N \cdot HBr_3$) were added thereto resulting immediately in a clear solution. 660 mg of sodium nitrite (9.5 mmol) were introduced in five equal portions over a period of about 15 minutes, followed by additional stirring for 30 minutes and then a solution of 1 g of sodium metabisulfite in 20 ml of water was added with stirring whereupon the pH was increased to 5.0 by careful addition of 4N sodium hydroxide. Acetonitrile was removed azeotropically by concentration at about 15 mm Hg over about 10 minutes and the resulting solution was acidified with 4N hydrochloric acid to a pH of 2.0 followed by three extractions with about equal volumes of ethyl acetate. The combined extract was dried over anhydrous magnesium sulfate, filtered and completely evaporated in vacuo and after extensive drying in vacuo, the obtained solid weighed 2.61 g.

According to the PMR spectrum of the product ($d_6$-DMSO, 60 Mc); it contained 6,6-dibromopenicillanic acid 1,1-dioxide, 6-α-bromo-penicillanic acid-1,1-dioxide, ethyl acetate and pyridine substance (pyridine itself and/or pyridine.HCl or pyridine.HBr) in 13:1:1.5:3.5 molar ratio. Assuming that pyridine is present as such, the calculated maximum yield is 78.7% of useful products. Taking into consideration the very low level of present degradation products as indicated by the PMR spectrum and by thin-layer chromatography and the possibility that pyridine is present as a salt, the estimated actual yield was about 65–70%.

STEP B:

2.5 g of the crude mixture of bromo-compounds prepared in Step A were suspended with stirring in an ice-cold mixture of 20 ml of water and 10 ml of acetonitrile. Addition of 4N sodium hydroxide resulted in a clear solution at pH 5.2 and then 2 g of zinc powder were added with vigorous stirring. At 0°–10° C., 4N hydrochloric acid was introduced gradually resulting in a fast reduction of pH to 3.5–4.0 and after about 20 minutes, the conversion was apparently completed as was proved by thin-layer chromatography. Excess zinc was removed by filtration and was washed with water. The combined filtrate was somewhat concentrated in vacuo to remove acetonitrile and the remaining solution in water was extracted repeatedly with ethyl acetate at pH 2. The combined extracts were washed with a small volume of an aqueous saturated sodium chloride solution, dried over anhydrous magnesium sulfate and filtered. The filtrate was evaporated in vacuo and dried extensively in vacuo to obtain 1.1 g of a slightly colored solid.

Analysis of the product by thin-layer chromatography indicated good purity. According to the PMR spectrum of the isolated product, it consisted of penicillanic acid 1,1-dioxide, one unknown by-product and ethyl acetate in 13:0.7:0.8 molar ratio which means a purity of at least 90% by weight or about 1.0 g of desired product starting from 2.0 g of starting material and an overall yield of about 55%.

Identification by PMR ($d_6$-DMSO, δ-values in ppm. TMS, 60 Mc); $C(CH_3)_2$; 1.36 (s, 3H) and 1.48 (s, 3H); $C_6$-$H_2$; between 3.08 and 3.9 (octet, $J_{AB}$ 16.2 cps, 2H, $J_{5-6}$ 1.9 cps visible in the high field half and $J_{5-6}$ 4.2 cps visible in the low field half of the splitting pattern), $C_3$-H:4.27 (s 1H) and $C_5$-H: about 5.15 (narrow quartet, $J_{5-6}$ values of about 1.9 and 4.2 cps, 1H).

A crude mixture of bromo-compounds (but somewhat more purified than the mixture of Step A) prepared according to Example 1b of the copending U.S. patent application filed on even date herewith was likewise reduced with zinc employing conditions somewhat more appropriate to the excess of dibromide present, i.e. reduction at 0°–5° C. and at pH 4.2 to 4.7. The isolated crude penicillanic acid 1,1-dioxide was more pure than obtained heretofore with an actual overall yield of at least 60%.

EXAMPLE 2

Reduction of a crude mixture of the bromo compounds

The starting material consisted of the bromo-compounds obtained by diazotisation-bromination of 6-β-amino-penicillanic acid 1,1-dioxide according to Example XI of the application filed on even date herewith. After the diazotization-bromination step, acetonitrile was removed in vacuo followed by extractions with dichloromethane and ethyl acetate. The combined ethyl acetate extract was twice washed with a small volume of saturated sodium chloride solution and mixed with 150 ml of cold water whereupon the pH was brought to 3.5 by addition of 4N sodium hydroxide.

The mixture was vigorously stirred at 10° C. and 5 g of zinc powder were added in four portions over 15 minutes while 4N hydrochloric acid was added dropwise at such a rate that the pH stayed between 3.5 and 4.0. Thereafter, 3 g of zinc powder were added and stirring was continued for about 20 minutes until pH correction was no longer necessary. Zinc was removed by filtration through a glass filter reinforced with filter-aid and was washed with water and ethyl acetate. The combined filtrate was brought to pH 2.0 with 4N hydrochloric acid whereupon the layers were separated and the aqueous layer was extracted four times with 150 ml of ethyl acetate, after which the combined extract was washed twice with a small volume of saturated sodium chloride solution, dried over anhydrous magnesium sulfate and was filtered. The filtrate was evaporated in vacuo and dried extensively at 0.5 mm Hg to obtain 10.0 g of a slightly colored, largely crystalline product. TLC and the PMR spectrum showed excellent quality with respect to the presence of unknown degradation products.

EXAMPLE 3

Reduction of 6,6-dibromo and 6-α-bromo-penicillanic acid-1,1-dioxide with zinc and hydrochloric acid compared with reduction with zinc in a phosphate-citrate buffer The same amount of the same, not completely pure mixture of 6,6-dibromo-penicillanic acid-1,1-dioxide and of a much smaller amount of 6-α-bromo-penicillanic acid-1,1-dioxide was used in both experiments. For as far as possible, the reaction conditions and the isolation procedure were kept alike.

(a) A pH 3.6 phosphate/citrate buffer was prepared according to McIlvain starting from 68 ml of an 0.1 molar (21 g per liter) solution of citric acid in water and 32 ml of an 0.2 molar (35.6 g per liter) solution of $Na_2HPO_4 \cdot 2H_2O$ in water and the actually was close to 3.6.

At 6° C., a suspension of 3.0 g of the crude mixture of bromides originating from an homogenized mixture of isolates of several diazotization-bromination experiments, in 10 ml of ethyl acetate was mixed with vigorous stirring with 100 ml of the above prepared buffer resulting in a pH 3.0. From the 6 g of zinc powder, a small portion was added immediately, expecting a quick rise in the pH. Since this did not happen, the pH was raised to 3.5 by addition of a few drops of 4N sodium hydroxide directly followed by introduction of more zinc. After the introduction of about 3 g of zinc, the pH rose to 4.0 continuously operating at 6° C. Next, the remaining amount of zinc was added in one portion and there was no rise of temperature during the reduction. A thin-layer chromatogram prepared 30 minutes after the beginning showed complete conversion of the starting material, but not in a clean fashion as the plate indicated much degradation. The mixture was filtered through glass and the unreacted zinc was washed with water. The combined filtrates with a pH of 4.0 were adjusted to pH 2.0 by addition of 4N hydrochloric acid and then was extracted four times with 50 ml volumes of ethyl acetate as checked with TLC resulting in complete removal of penicillanic acid-1,1-dioxide from water. After washing with 10 ml of a saturated sodium chloride solution, the combined extract was stirred in an ice-bath with anhydrous magnesium sulfate and 0.5 g of activated carbon. After filtration and washing of the filter cake with ethyl acetate, the combined still colored filtrate was evaporated in vacuo followed by extensive drying in vacuo to obtain 0.820 g of colored product. If the product had been pure, the yield would have been 50%, taking into account the composition and the purity of the starting material.

According to the PMR spectrum of the product, it contained 5 mol % of citric acid and 10 mol % of ethyl acetate. Since other impurities were present too, the actual yield of penicillanic acid-1,1-dioxide was certainly not more than 40%.

(b) 45 ml of iced water were added with stirring to a suspension of 3.0 g of the same starting material in 10 ml of ethyl acetate cooled in ice followed by careful addition of 4N sodium hydroxide until complete dissolution at pH 4.0. Of the 6 g of zinc powder, a small portion was added with vigorous stirring, immediately followed by introduction of 4N hydrochloric acid to pH 3.5. Maintaining the reaction temperature close to 6° C., about half of the amount of zinc was added over 15 minutes while keeping the pH at 4.0 by addition of 4N hydrochloric acid. After 15 minutes reaction, the remaining zinc was added in one portion. As under (a), stirring was disrupted after 30 minutes from the start though the conversion was completed after 20 minutes. TLC showed complete disappearance of the bromides, but also a much more selective formation of penicillanic acid-1,1-dioxide as compared with experiment (a). The spot at the start of the plate, relating to very polar degradation products, was relatively much smaller, and in contrast with the product of experiment (a), an impurity less polar than the desired compound having a greater Rf value was now not present. The reaction mixture was treated as described above. The final filtrate was less colored, as was the crystalline final product. The yield of 1.48 g was considerably more than obtained above. If the product had been pure, the yield would have been 90.2%. Compared with the product of experiment (a), the appreciably better quality of product (b) allowed for a determination of the content of penicillanic acid-1,1-dioxide by PMR which determination gave a purity of 91% by weight. This means a yield of 82.1%, at least twice as much as reached in experiment (a).

By a more diversified extraction procedure, it would have been possible to obtain a more pure product from experiment (a) and a virtually pure product from experiment (b), but such a procedure could have resulted in some losses, eventually leading to a probably still larger difference in the amounts of isolated product. The starting material contained the dibromide and the monobromide in about a 9:1 ratio.

EXAMPLE 4

Comparison of reduction of 6,6-dibromo and 6-α-bromo-penicillanic acid-1,1-dioxide with zinc and hydrohalogenic acids with reduction with zinc in phosphate buffer The starting material was prepared as follows: A number of isolates obtained from various small scale experiments like those described in Examples 8 and 9 of the U.S. patent application filed on even date herewith were combined and thereafter suspended in a mixture of ethyl acetate and water. Dilute sodium hydroxide was added until complete dissolution of starting material occured and the layers were separated at a pH of 6.5. The organic layer was discarded and the aqueous layer was extracted at pH 2.5 with ethyl acetate. The combined extracts were washed twice with a small volume of saturated sodium chloride solution, dried over magnesium sulfate and filtered. The filtrate was evaporated in vacuo and dried in vacuo to obtain a homogeneous and relatively pure mixture of bromides with the dibromide in large excess over the monobromide which was analyzed by means of PMR involving addition of a weighed out amount of an internal reference. Of this starting material for the following reduction experiments, the exact content and the molar dibromide/monobromide ratio were thereby determined in this manner.

(a) 5 g of the above indicated mixture of bromides were suspended with stirring and cooling in ice in a mixture of 20 ml of ethyl acetate and 40 ml of a phosphate buffer prepared by addition of 10% phosphoric acid to a solution of 35.6 g of $Na_2HPO_4.2H_2O$ in 1 liter of distilled water until pH 6.5. The starting material went into solution resulting in pH 4.0 of the clear mixture and dilute phosphoric acid was added until the mixture attained a pH of 3.5. At 4° C., 5 g of zinc were added over 5 minutes which did not result in any change in pH or temperature. After addition of 5 g of zinc, once more the temperature was raised to 6° C. and reaction was now indicated by a slight drop in the pH and a small rise in temperature. The reaction was disrupted after about 15 minutes with additional stirring at 6°-8° C. and TLC showed complete conversion of the starting material; the plate was similar to the one prepared in experiment (a) of Example 3, but indicated a slightly more selective reduction. The reaction mixture was treated in the same way as described in Example 3 to obtain 1.48 g of yellowish product which made a better impression than the material of Example 3, experiment (a). From a PMR spectrum taken from a mixture of weighed out amounts of isolated product and a reference compound, it could be calculated that the isolated product had a purity of 93.3% by weight with the major impurity being ethyl acetate (3.4% by weight) which means an actual yield of 1.381 g or 47.0%. The yield, though still rather low, as well as the quality of the product were substantially better than reached in experiment (a) of Example 17. Since the employed concentration of starting material was not identical in both experiments, it can not be concluded that citrate anions are even more deleterious than phosphate anions.

(b) This experiment was an exact as possible repetition of experiment (a) except for one deliberate variation in which 1 g of sodium bromide was added to the phosphate buffer to establish whether halogen anions could have a catalyzing effect and/or could reduce the obviously deleterious effect of phosphate anions. This was however not apparent from the course of the reduction, nor from TLC, nor from yield and quality of the isolated product which was 1.40 g. Purity determined by means of PMR was only 71.8% by weight which means an actual yield of only 0.997 g or 33.9%.

From the experiments of Examples 3 and 4, it is quite clear that phosphate buffers should not be employed in contrast to recommendations proposed in the prior art. From a purely scientific standpoint, it could be argued that an increase of ionic strength, such as is apparent in a comparison of experiments (a) and (b) of the present Example, could enlarge the relative share of undesired side reactions, in one way or the other associated with or triggered by a nucleophilic substitution event. In part, this may be the case, but then only in part.

During experimentation in the development of the present invention, it was experienced that reduction applied immediately after preparation of the bromide compounds, thus without intermediate extraction of bromides with ethyl acetate followed by mixing with water, etc. could result in maximal about 20% lower yields i.e., with the same auxiliary agent 45–50% overall yield instead of 55–60%, as well as in the necessity of employing relatively more zinc as compared with the procedure involving intermediate extraction. However, under such conditions the ionic strength is still greater than applied in the phosphate buffer experiments of Examples 3 and 4 while there may be other origins for the occasionally lower yields of directly applied reductions such as the presence of substantially more degradation products.

(c) 5 g of the same starting material were suspended with cooling in ice in a mixture of 20 ml of ethyl acetate and 50 ml of cold water and 4N sodium hydroxide was added until complete dissolution at pH 5. About 4N hydrobromic acid was dropped in until the vigorously stirred mixture attained a pH of 3.8 at 4° C. 4 g of zinc powder were introduced gradually in four portions over 15 minutes while dilute hydrobromic acid was added dropwise to maintain the pH at 3.5-4. In the beginning, the temperature rose to 10° C. but settled to 6°–8° C. later on and after introduction of the last portion of zinc, the pH soon became constant indicating complete conversion. There was no reason for addition of more zinc, but to imitate the conditions of experiments (a) and (b), the mixture was stirred for another 15 minutes at 8°–10° C. and the usual isolation procedure was followed to obtain 2.46 g. If pure, this means a yield of 90.1%. PMR indicated a purity very close to 100% and the actual yield therefore was at least 89%.

(d) This experiment was carried out in somewhat lower concentration as compared with experiment (a) and involved addition of sodium chloride to the phosphate buffer. The ingredients were 3 g of the same mixture of bromides, 20 ml of ethyl acetate, 40 ml of the phosphate buffer, 200 mg of sodium chloride, diluted phosphoric acid for acidification of the mixture to pH 3.7. During the reaction, the temperature was directly brought to 6°–8° C. and 3 g of zinc powder were added in four portions over 15 minutes. Thereafter, 2 g of zinc powder were added in one portion, followed by 15 minutes of additional stirring at 6°–10° C. TLC indicated complete conversion, but also much degradation to obtain 0.820 g of semi-solid product, or 46.5% if 100% pure. TLC indicated somewhat less purity as compared with the product of experiment (a) and the actual yield was estimated to be 40-42%.

EXAMPLE 5

Comparison of reduction of 6,6-dibromo- and 6-α-bromo-penicillanic acid 1,1-dioxides with zinc and sulfuric acid and with zinc in phosphoric acid Since the poor results of reduction with zinc powder in phosphate buffers as shown in the preceding two Examples to some extent could have been caused by the relative high ionic strength in buffers, dilute phosphoric acid was used in the present Example compared with sulfuric acid. The starting material was prepared in a larger scale experiment and used without further purification and it contained 84.5% by weight of the dibromide and 6.0% of the monobromide. 5 g of this product was therefore present as 11.77 mmol of useful compound.

(a) 4N NaOH was added dropwise with stirring to a suspension of 5 g of the crude mixture of bromides in 20 ml of ethyl acetate and 50 ml of iced water until a clear solution was reached at pH 5.0. At 8° C., 10% phosphoric acid was added dropwise until the pH was 3.8 and 4 g of zinc powder were added in four equal portions over 15 minutes at 8°–10° C. As in the preceding Examples, it was noticed again that phosphate anions caused an initial lowering of the pH which was never noticed during reduction in the presence of halogen anions or sulfate anions. By gradual addition of 10% phosphoric acid, the pH was kept between 3.5 and 4.0 and after the addition of zinc, the mixture was stirred for another 30 minutes at 8°–10° C. After the usual manipulations, 1.88 g of heavily colored product was obtained. Like the starting material, this odorous product was submitted to quantitative analysis by PMR employing weighed amounts of the products and of 3,4,5-trimethoxyphenylacetic acid. If pure, the yield would have been 1.88/233/0.01177 times 100%=68.55%. However the PMR spectrum indicated a purity maximal of 58% as a consequence of the presence of several degradation products. The actual yield was therefore not better than at most 40%.

(b) Exactly the same experiment was carried out with 4N sulfuric acid to obtain 2.62 g or 95.54% if pure. Quantitative analysis by PMR indicated a purity by weight of at least 91% and the actual yield was therefore at least 87%.

EXAMPLE 6

Preparation of pivaloyloxymethyl penicillanate 1,1-dioxide

A solution of 2.50 g of a mixture of the pivaloyloxymethyl esters of 6,6-dibromo- and 6-α-bromo-penicillanic acid 1,1-dioxide prepared according to Example 21 of the application filed on even date herewith in 50 ml of acetonitrile was cooled to 2° C. 5 ml of cold water and 1.0 g of zinc powder were then added and then about 10 ml of 1N hydrochloric acid were introduced dropwise over 5–10 minutes, the rate being adjusted to a pH of not less than 2.5 and a temperature not higher than 8° C. After completion of the addition, the pH rose gradually to 6 and a thin-layer chromatogram prepared in the meantime showed a clean and complete conversion to the desired compound. The reaction mixture was subjected to filtration through a glass filter strengthened with filter-aid and including washing with acetonitrile. The volume of the combined, almost colorless filtrate was enlarged with 30 ml of cold water followed by azeotropic removal of acetonitrile in vacuo, resulting in the precipitation of an oil. The concentration in vacuo was then interrupted to introduce a seed crystal and on renewed concentration, the oil changed into a crystalline product which was collected by filtration, washed with cold water and extensively dried in vacuo in the presence of phosphorus pentoxide to obtain 1.59 g of according to TLC and the PMR spectrum, practically pure product. The yield was at least 88%, as the final product was definitively more pure than the starting material. The overall yield over steps (b) and (c) was 48.5%.

IR (KBr-disc, values in cm$^{-1}$): 2990 L (m), 1802 (vs), 1778 (vs), 1755 (vs), 1325 (vs), 1280 (m), 1200 (s), 1165 (s), 1110 (vs), 1000 (s), 982 (s).

PMR (CDCl$_3$, 60 Mc, δ-values in ppm, TMS): 1.22 (s, 9H), 1.43 (s, 3H), 1.59 (s, 3H), 3.45 (d, J=3.3 Hz, 2H), 4.39 (s, 1H), 4.62 (t, J=3.3 Hz, 1H), 5.65 to 6.00 (AB-q, $J_{AB}$=5.4 Hz, 2H).

EXAMPLE 7

Comparison of various acids in the reduction with zinc powder

In all experiments, there was used the same starting material, that is 3.6 g of a crude mixture of bromides directly obtained from an experiment on large scale involving the employment of caprolactam as auxiliary agent and due to non exhaustive elimination, the starting material contained a considerable remaining amount of caprolactam. The final products also obtained caprolactam in varying relative amounts and the actual content of bromides in the starting material was 3.2 g with a 4:3 molar ratio of the dibromide to the monobromide, or 5.12 mmol of the dibromide and 3.84 mmol of the monobromide for a total of 8.96 mmol of useful compounds. The theoretical yield of 100% pure product would then be 2.088 g. All the experiments involved reduction at 8°–10° C., a starting mixture of 50 ml of water and 20 ml of ethyl acetate, 2 g of zinc added in 15 minutes in 4 portions and 1 g of zinc added in one portion, followed by 30 minutes of additional stirring, except for the last two experiments, wherein stirring was continued during about 2 hours at appreciably higher pH than the pH 3.5 maintained in the first six experiments. Except for the last experiment, in which the acidic mixture was brought to a pH of 3.5 by addition of solid borax, the pH of the mixture in all other experiments was brought to 5 by addition of 4N NaOH before zinc and acid were introduced. In experiments 2-6, the acid was introduced as an about 10% solution in water. In experiments 7 and 8, the acid was added in solid form because of reduced solubility in water.

TABLE

| Exp. No. | Acid | pH interval | isolated weight | relative content of PAS | actual yield |
|---|---|---|---|---|---|
| 1 | 4N HCl | 3.5–4.0 | 2.24 g | 84.3% | 90.1% |
| 2 | oxalic acid | " | 2.00 g | 79.4% | 76.1% |
| 3 | malonic acid | " | 2.40* g | 61.6% | 70.8% |
| 4 | citric acid | " | 2.01 g | 90.2% | 86.8% |
| 5 | p-tolyl-sulfonic acid | " | 2.06 g | 73.3% | 72.3% |
| 6 | perchloric acid | " | 2.09 g | 76.7% | 76.8% |
| 7 | 4-chloro-benzoic acid | 4–5.5 | 1.80 g | 57.5% | 49.6% |
| 8 | boric acid | 3.5–6.0 | 1.67 g | 52.7% | 42.2% |

*The product was also contamined by malonic acid (about 14% by weight).
"PAS" is an abbreviation of penicillanic acid 1,1-dioxide

CONCLUSION

Phosphoric acid, boric acid and benzoic acid produce poor yields while the latter two also give practical difficulties. Perchloric acid, aryl sulfonic acids and sufficiently acidic alkanoic acids, alkanoic diacids and citric acid can be used in principle, but except for citric acid produce substantially less good yields as compared with hydrochloric acid, hydrobromic acid [cf. Example IV (a)] and sulfuric acid [cf. Example V (b)].

EXAMPLE 8

Using the procedure of Example 1, 10 g (90% purity-36.3 mmol) of 6-β-amino-penicillanic acid-1,1-dioxide was converted into a mixture of 6-α-bromo and 6,6-dibromo-penicillanic acid-1,1-dioxides followed by reduction at different pHs during the reduction. The experiment was repeated twice for each pH and the results are reported in the following Table.

| pH | % Yield of PAS |
|---|---|
| 2.0 | 27% (52% unreacted starting material) |
| 3.5–4.0 | 62% |
| 6.5 | 5% (37% unreacted starting material) |

Various modifications of the process of the invention may be made without departing from the spirit or scope thereof and it should be understood that the invention is intended to be limited only as defined in the appended claims.

What we claim is:

1. A process for the preparation of penicillanic acid 1,1-dioxides of the formula

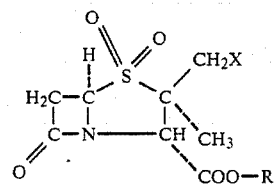

II wherein X is selected from the group consisting of hydrogen, halogen and aceoxy and R is selected from the group consisting of hydrogen, a pharmaceutically acceptable metal ion and a pharmaceutically acceptable ester radical comprising debrominating 6-α-bromoand/or 6,6-dibromo-penicillanic 1,1-dioxides selected from the group consisting of the formula

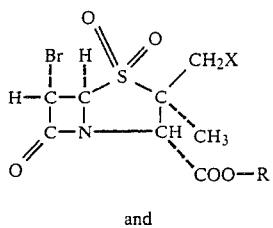

and

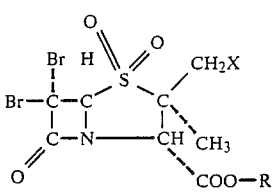

wherein X and R have the above definition in an aqueous containing medium with zinc in association with an acid having a $pK_a$-value measured in water less than 3.5 and optionally if R is H converting the acid into a pharmaceutically acceptable salt or a pharmaceutically acceptable ester.

2. The process of claim 1 wherein the aqueous medium contains an inert organic solvent.

3. The process of claim 2 wherein the inert organic solvent is selected from the group consisting of acetonitrile, methyl acetate and ethyl acetate.

4. The process of claim 1 wherein the pH at which the debromination is effected is 2.5 to 6.

5. The process of claim 4 wherein the pH is 3 to 5.

6. The process of claim 1 wherein the reduction with zinc is effected in association with dilute hydrochloric acid, hydrobromic acid or sulfuric acid.

7. The process of claim 1 wherein the reaction is performed at a temperature between 0° and 20° C.

8. The process of claim 1 wherein the reaction is performed at a temperature between 0° and 10° C.

9. The process of claim 1 wherein an amount of 1.2 to 2 moles of zinc is used for each bromine atom present in the starting compounds.

10. The process of claim 1 wherein R is H and the penicillanic acid-1,1-dioxide obtained is coverted into its sodium or potassium salt.

* * * * *